(12) United States Patent
Xu

(10) Patent No.: US 10,039,775 B2
(45) Date of Patent: Aug. 7, 2018

(54) PREPARATION METHOD FOR ANTITUMOR DRUG AP26113

(71) Applicant: SUZHOU MIRACPHARMA TECHNOLOGY CO., LTD., Suzhou (CN)

(72) Inventor: Xuenong Xu, Suzhou (CN)

(73) Assignee: SUZHOU MIRACPHARMA TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 15/822,092

(22) Filed: Nov. 24, 2017

(65) Prior Publication Data

US 2018/0071324 A1 Mar. 15, 2018

Related U.S. Application Data

(63) Continuation of application No. PCT/CN2016/090408, filed on Jul. 19, 2016.

(30) Foreign Application Priority Data

Jul. 27, 2015 (CN) .......................... 2015 1 0444071

(51) Int. Cl.
*A61K 31/675* (2006.01)
*C07F 9/6558* (2006.01)

(52) U.S. Cl.
CPC .......... *A61K 31/675* (2013.01); *C07F 9/6558* (2013.01)

(58) Field of Classification Search
CPC ..................................... C07F 9/6558
USPC ............................................... 544/323
See application file for complete search history.

(56) References Cited

U.S. PATENT DOCUMENTS

| 2013/0225527 A1 | 8/2013 | Wang et al. |
| 2013/0225528 A1 | 8/2013 | Wang et al. |
| 2014/0066406 A1 | 3/2014 | Wang et al. |

FOREIGN PATENT DOCUMENTS

| CN | 102105150 A | 6/2011 |
| CN | 105061506 A | 11/2015 |
| WO | 03000186 A2 | 1/2003 |
| WO | 2009143389 A1 | 11/2009 |

*Primary Examiner* — Deepak R Rao
(74) *Attorney, Agent, or Firm* — Perkins Coie LLP

(57) ABSTRACT

Disclosed is a preparation method for an antitumor drug AP26113 (I). The method comprises the following preparation steps: cyclizing N-[2-methoxyl-4[4-(dimethyl amino) piperid-1-yl]aniline]guanidine and N,N-dimethylamino acrylate, condensing N-[2-methoxyl-4[4-(dimethyl amino) piperid-1-yl]aniline]guanidine and 4-(dimethyl phosphitylate)aniline, and chlorinating N-[2-methoxyl-4[4-(dimethyl amino)piperid-1-yl]aniline]guanidine and a chlorinating agent, sequentially, so as to prepare AP26113 (I). The preparation method adopts easily-obtained raw materials, causes few side reactions, and is economical, environmentally friendly, and suitable for industrial production.

19 Claims, No Drawings

PREPARATION METHOD FOR ANTITUMOR DRUG AP26113

CROSS REFERENCE TO RELATED APPLICATIONS

This application is a continuation of PCT/CN2016/090408 filed 2016 Jul. 19, which claims priority to CN 2015104440715 filed 2015 Jul. 27, both of which are incorporated herein by reference.

TECHNICAL FIELD

The invention belongs to the technical field of organic synthetic route design and preparation of a crude drug and an intermediate therefor, and particularly relates to a preparation method for an antitumor drug AP26113.

BACKGROUND ART

AP26113 is an experimental drug of a targeted small molecular tyrosine kinase inhibitor developed by the Ariad Pharmaceuticals Company, and is used for treating patients suffering from anaplastic lymphoma kinase positive (ALK) metastatic nonsmall cell lung cancer (NSCLC) which resists crizotinib. The drug was granted as a breakthrough therapy drug by Food and Drug Administration (FDA) in August 2014. According to clinical data at present, AP26113 has continuous anti-tumor activity on patients suffering from the ALK positive nonsmall cell lung cancer, including brain metastases patients. Moreover, the inhibitory activity of AP26113 to ALK is about 10 times of the inhibitor activity of the crizotinib to ALK, and all nine identified crizotinib resistant ALK mutation can be inhibited.

The chemical name of AP26113 is 5-chloro-N2-[4-[4-(dimethyl amino)-1-piperidyl]-2-methoxyphenyl]-N4-[2-(dimethyl phosphitylate)phenyl]-2,4-diaminopyrimidine (I), and a structural formula thereof is as follows:

AP26113 (I)

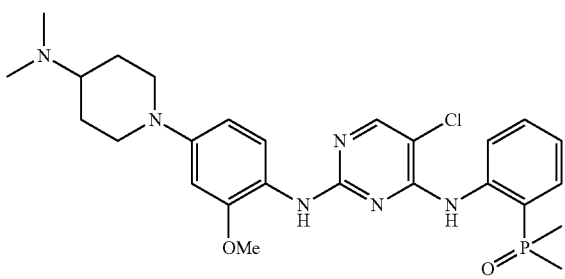

A preparation method for AP26113 has been researched and reported, and PCT patent WO2009143389 of the Ariad Company and United States patents US20130225527, US20130225528 and US20140066406 have reported a preparation method for AP26113 and raw materials A and B therefor. According to the method, 2,4,5-trichloropyrimidine and the raw material A are subjected to substitution reaction on a pyrimidine ring and then the 2,4,5-trichloropyrimidine and the raw material B are subjected to substitution reaction on the pyrimidine ring to obtain the target compound AP26113.

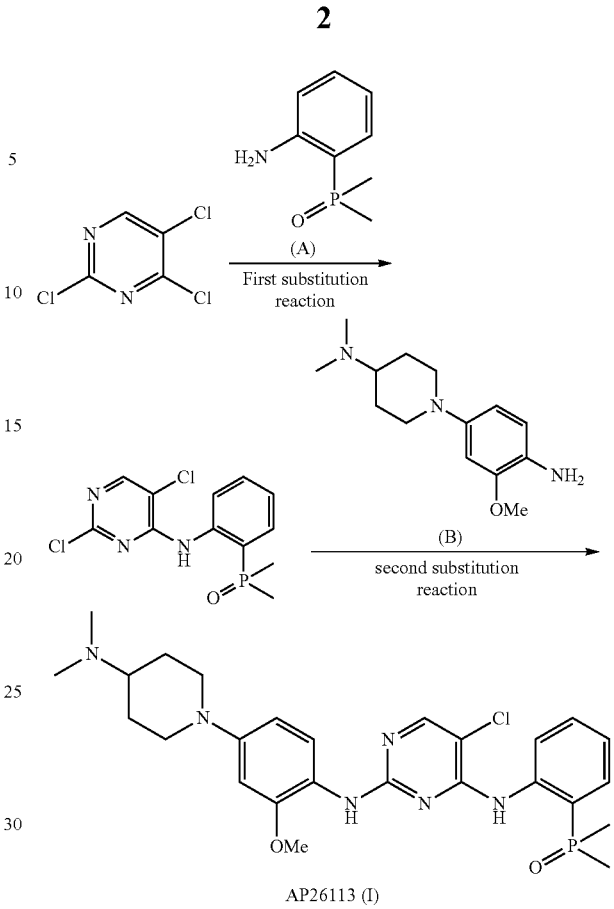

AP26113 (I)

By analysis of the above synthetic routes, although synthetic steps are simple comparatively, difference of nucleophilic activities of three helium atoms on the 2,4,5-trichloropyrimidine is limited, the regioselectivity is inevitably interfered in the face of the same or similar anilines groups, unnecessary side reactions are caused, and thus, the quality of a product is affected. Meanwhile, by use of a precious metal palladium reagent in a reaction process, the manufacturing cost is increased to some extent, and industrialization is not facilitated.

Therefore, use of a modern synthetic technology, use of easily-obtained raw materials, design and development of a simple, speedy, economical and environment-friendly new synthetic route which facilitates industrialization, and particularly overcoming of side reactions caused by regioselectivity on the pyrimidine ring play an important role in economic and technical development of the drug.

SUMMARY OF THE INVENTION

The invention aims to design a novel synthetic route which introduces functional groups step by step to avoid side reactions so as to overcome shortcomings in the prior art. A preparation method for AP26113, obtained through the synthetic route, has the advantages of easily-obtained raw materials, few side reactions, economy, environmental friendliness, suitability for industrial production and the like.

In order to achieve the above objective, the invention adopts the following main technical solution: a preparation method for an antitumor drug AP26113 (I),

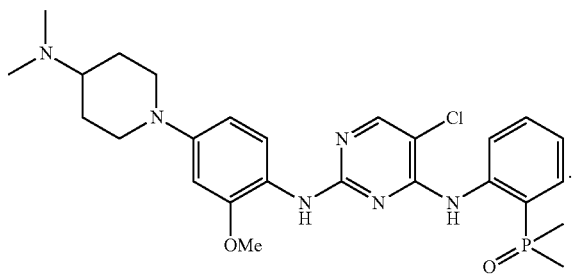

AP26113 (I)

The preparation method for the antitumor drug AP26113 (I) comprises the following synthetic steps: carrying out cyclization reaction on N-[2-methoxyl-4[4-(dimethyl amino)piperid-1-yl]aniline]guanidine (II) and N,N-dimethylamino acrylate to prepare N2-[4-[4-(dimethyl amino)-1-piperidyl]-2-methoxyphenyl]amino-4(1H)-pyrimidone (III); carrying out condensation reaction on the N2-[4-[4-(dimethyl amino)-1-piperidyl]-2-methoxyphenyl]amino-4(1H)-pyrimidone (III) and 4-(dimethyl phosphitylate)aniline (A) under the effects of a condensating agent and an alkali accelerator to prepare N2-[4-[4-(dimethyl amino)-1-piperidyl]-2-methoxyphenyl]-N4-[2-(dimethyl phosphitylate)phenyl]-2,4-diaminopyrimidine (IV); and carrying out chlorination reaction on the N2-[4-[4-(dimethyl amino)-1-piperidyl]-2-methoxyphenyl]-N4-[2-(dimethyl phosphitylate)phenyl]-2,4-diaminopyrimidine (IV) and a chlorinating agent to prepare AP26113 (I).

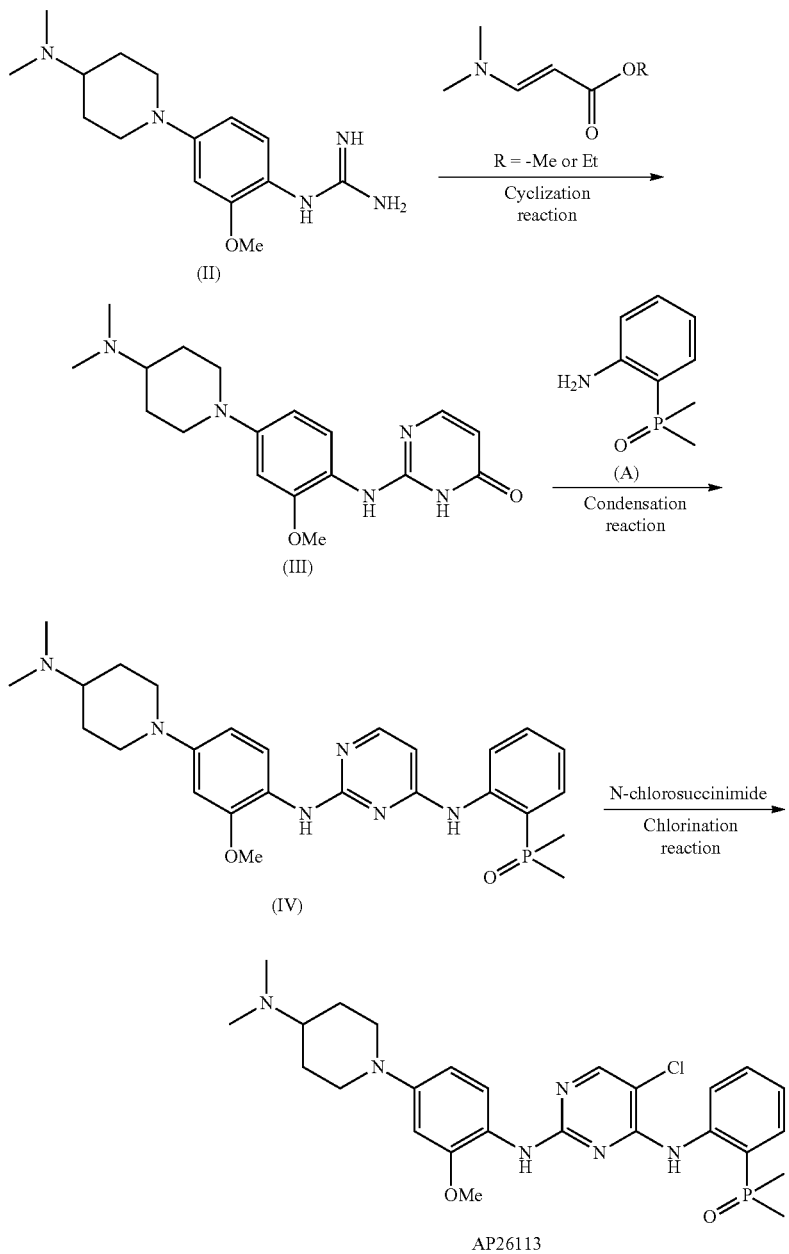

In addition, the invention further proposes the following subordinate technical solution.

The N,N-dimethylamino acrylate used for the cyclization reaction is N,N-dimethylaminomethyl acylate or N,N-dimethylaminoethyl acrylate.

A molar ratio of the raw materials including the N-[2-methoxyl-4[4-(dimethyl amino)piperid-1-yl]aniline]guanidine (II) and the N,N-dimethylamino acylate for the cyclization reaction is 1:1-2, and is 1:1.3-1.5 preferably.

A solvent of the cyclization reaction is methylbenzene, dimethylbenzene, dioxane, acetonitrile, N,N-dimethylformamide, N,N-dimethylacetamide or dimethylsulfoxide, and is methylbenzene or N,N-dimethylformamide preferably.

A temperature of the cyclization reaction is 50-150° C., and is 110-140° C. preferably.

The condensating agent of the condensation reaction is N,N'-dicyclohexylcarbodiimide, carbonyldiimidazole, N,N'-diisopropylcarbodiimide, 1-hydroxy-benzotriazole, 2-(1H-benzotriazole-1-yl)-1,1,3,3-tetramethyluronium tetrafluoroborate, O-(7-azabenzotriazol-1-yl)-N,N,N',N'-tetramethyluronium hexafluorophosphate, O-benzotriazol-1-yl-tetramethyluronium hexafluorophosphate or (benzotriazollyloxy)tris(dimethylamino)phosphonium hexafluophosphate, and is O-benzotriazol-1-yl-tetramethyluronium hexafluorophosphate or (benzotriazollyloxy)tris(dimethylamino)phosphonium hexafluophosphate preferably.

The alkali accelerator of the condensation reaction is triethylamine, pyridine, 2,6-dimethyl pyridine, 4-dimethylaminopyridine, N-methylmorpholine, N-ethylmorpholine, diisopropylethylamine, 1,5-diazabicyclo[4.3.0]-non-5-ene (DBN), 1,8-diazabicyclo[5.4.0]-undeca-7-ene or 1,4-diazabicyclo-[2.2.2]octane, and is 1,8-diazabicyclo[5.4.0]-undeca-7-ene or 1,5-diazabicyclo[4.3.0]non-5-ene or 1,4-diazabicyclo-[2.2.2]octane preferably.

The solvent of the condensation reaction is methylbenzene, dimethylbenzene, ethyl acetate, isopropyl acetate, butyl acetate, chloroform, dimethylsulfoxide, N,N-dimethylformamide or acetonitrile, and is acetonitrile preferably.

A temperature of the condensation reaction is 0-120° C., and is 50-60° C. preferably.

The chlorinating agent of the chlorination reaction is N-chlorosuccinimide or 1,3-dichloro-5,5-dimethylhydantoin, and is N-chlorosuccinimide preferably.

A solvent of the chlorination reaction is tetrahydrofuran, dioxane, acetonitrile, dichloromethane, chloroform or methylbenzene, and is acetonitrile preferably.

A temperature of the chlorination reaction is 0-70° C., and is 20-30° C. preferably.

Meanwhile, the invention further provides a preparation method for the raw material N-[2-methoxyl-4[4-(dimethyl amino)piperid-1-yl]aniline]guanidine (II), namely, the N-[2-methoxyl-4[4-(dimethyl amino)piperid-1-yl]aniline]guanidine (II) is prepared by carrying out guanidination reaction on 2-methoxyl-4[4-(dimethyl amino)piperid-1-yl]aniline (B) and hydrogen cyanamide.

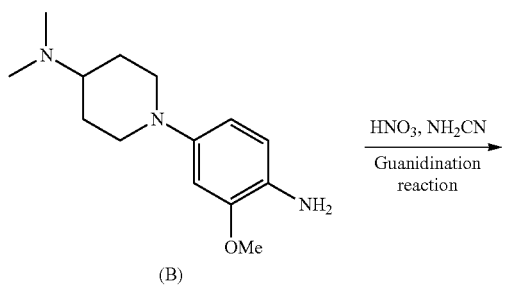

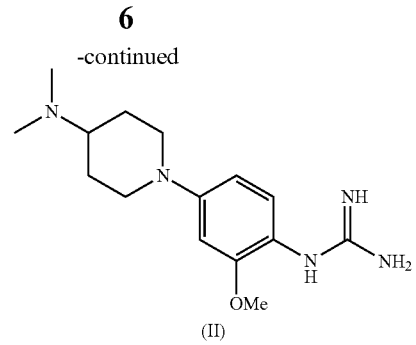

A molar ratio of the raw materials including the 2-methoxyl-4[4-(dimethyl amino)piperid-1-yl]aniline (B) and the hydrogen cyanamide for the guanidination reaction is 1:1-2, and is 1:1.2-1.6 preferably.

A solvent of the guanidination reaction is benzene, methylbenzene, methanol, ethanol, N,N-dimethylformamide or dioxane, and is methanol or dioxane preferably.

A temperature of the guanidination reaction is 25-120° C., and is 50-70° C. preferably.

Compared with the prior art, the preparation method for the AP26113 (I), involved in the invention has the advantages of easily-obtained raw materials, few side reactions, environmental friendliness, economy and the like, therefore, industrialization production of the crude drug is facilitated, and development of the economic technology of the crude drug is promoted.

DETAILED DESCRIPTION OF THE INVENTION

The technical solution of the invention will be further described in detail in a non-limiting manner with reference to several preferred examples below. Preparation of raw materials including 4-(dimethyl phosphitylate)aniline (A) and 2-methoxyl-4[4-(dimethyl amino)piperid-1-yl]aniline (B) can refer to a preparation method in PCT patent WO2009143389 filed on May 21, 2009 and named as 'PHOSPHOROUS DERIVATIVES AS KINASE INHIBITORS'.

Example 1

2-methoxyl-4[4-(dimethyl amino)piperid-1-yl]aniline (B) (24.9, 0.1 mol) and methanol 250 mL were added in a reaction bottle, were cooled to a temperature of 0° C. by ice bath, 60-65% concentrated nitric acid (15 mL, 0.15 mol) and 50% hydrogen cyanamide solution (10 mL, 0.15 mol) were successively added, heating was carried out till refluxing, and stirring reaction was carried out for 12-14 hours while to finish TLC detection reaction. Cooled to a temperature of 0-5° C. was carried out, 250 mL of methyl tertiary-butyl ether was added in reaction fluid, then solid was separated out, the solid was filtered, was washed with water and cold acetonitrile successively, and was dried to obtain brown solid N-[2-methoxyl-4[4-(dimethyl amino)piperid-1-yl]aniline]guanidine (II) 16.3 g, the yield was 56.0%, and FAB-MS m/z: 292[M+H]$^+$.

Example 2

N-[2-methoxyl-4[4-(dimethyl amino)piperid-1-yl]aniline]guanidine (II) (2.9 g, 10 mmol), N,N-dimethylaminomethyl acrylate (1.8 g, 13.7 mmol) and methylbenzene 50 mL were added in a reaction bottle, were heated till refluxing, and were subjected to stirring reaction for 24-26 hours to finish TLC detection reaction. Cooling to room temperature was carried out, and then solid was separated out. The solid was filtered, a filter cake was washed with cold methanol, and was dried under vacuum to obtain off-white solid N2-[4-[4-(dimethyl amino)-1-piperidyl]-2-methoxyphenyl]amino-4(1H)-pyrimidone (III) 2.65 g, the yield was 77.3%, and FAB-MS m/z: 344 [M+H]$^+$.

Example 3

N-[2-methoxyl-4[4-(dimethyl amino)piperid-1-yl]aniline]guanidine (II) (2.9 g, 10 mmol), N,N-dimethylaminoethyl acrylate (2.0 g, 14.0 mmol) and N,N-dimethylformamide 30 mL were added in a reaction bottle, were heated to a temperature of 115-125° C., and were subjected to stirring reaction for 22-24 hours to finish TLC detection reaction. Concentration under reduced pressure was carried out, obtained residues were added with 50 mL of ethanol, and were cooled to room temperature while stirring, and then solid was separated out. The solid was filtered, a filter cake was washed with cold ethanol, and was dried under vacuum to obtain off-white solid N2-[4-[4-(dimethyl amino)-1-piperidyl]-2-methoxyphenyl]amino-4(1H)-pyrimidone (III) 2.73 g, the yield was 79.6%, and FAB-MS m/z: 344 [M+H]$^+$.

Example 4

Under protection of nitrogen, N2-[4-[4-(dimethyl amino)-1-piperidyl]-2-methoxyphenyl]amino-4(1H)-pyrimidone (III) (3.43 g, 10 mmol), (benzotriazollyloxy)tris(dimethylamino)phosphonium hexafluophosphate (6.63 g, 15 mmol) and acetonitrile 100 mL were added in a three-necked flask. 1,8-diazabicyclo[5.4.0]-undeca-7-ene (DBU) (2.28 g, 15 mmol) was dropwise added during stirring, and reaction was carried out for 12 hours at room temperature after dropwise adding was finished. Heating to a temperature of 60° C. was carried out, and reaction was continued for 12 hours. Distillation under reduced pressure was carried out to remove a solvent, dissolving with 100 mL of ethyl acetate was carried out, washing with 20 mL of 2M sodium hydroxide and 20 mL of water was carried out, after an organic phase was dried with anhydrous sodium sulfate, 4-(dimethyl phosphitylate)aniline (A) (2.2 g, 13 mmol) dissolved with 50 mL of tetrahydrofuran and a solution of sodium hydride (0.31 g, 13 mmol) was added, heating to a temperature of 50-55° C. was carried out, and stirring reaction was carried out for 6-8 hours to finish TLC monitoring reaction. Quenching reaction was carried out with a saturated salt solution to separate out the organic phase, the organic phase was dried, and was distilled under reduced pressure to recycle a solvent, a crude product was recrystallized with ethanol to obtain off-white solid N2-[4-[4-(dimethyl amino)-1-piperidyl]-2-methoxyphenyl]-N4-[2-(dimethyl phosphitylate)phenyl]-2,4-diaminopyrimidine (IV) 4.1 g, and the yield was 83.2%. FAB-MS m/z: 495 [M+H]$^+$.

Example 5

Under protection of nitrogen, N2-[4-[4-(dimethyl amino)-1-piperidyl]-2-methoxyphenyl]amino-4(1H)-pyrimidone (III) (3.43 g, 10 mmol), (benzotriazollyloxy)tris(dimethylamino)phosphonium hexafluophosphate (BOP) (6.63 g, 15 mmol), 4-(dimethyl phosphitylate)aniline (A) (2.2 g, 13 mmol) and N,N-dimethylformamide 100 mL were added in a three-necked flask. 1,8-diazabicyclo[5.4.0]-undeca-7-ene (DBU) (2.28 g, 15 mmol) was dropwise added during stirring, and reaction was carried out for 12 hours at room temperature after dropwise adding was finished. Heated to a temperature of 60° C. was carried out, and reaction was continued for 12 hours. Distillation under reduced pressure was carried out to remove a solvent, dissolving by adding 100 mL of ethyl acetate was carried out, and washing with 20 mL of 2M sodium hydroxide was carried out. An organic phase was separated out, dried, and concentrated under reduced pressure. Residues were recrystallized with ethanol to obtain off-white solid N2-[4-[4-(dimethyl amino)-1-piperidyl]-2-methoxyphenyl]-N4-[2-(dimethyl phosphitylate)phenyl]-2,4-diaminopyrimidine (IV) 2.4 g, and the yield was 48.6%. FAB-MS m/z: 495 [M+H]$^+$.

Example 6

N2-[4-[4-(dimethyl amino)-1-piperidyl]-2-methoxyphenyl]-N4-[2-(dimethyl phosphitylate)phenyl]-2,4-diaminopyrimidine (IV) (4.9 g, 10 mmol) and acetonitrile 100 mL were added in a dry reaction bottle, and were stirred and dissolved at room temperature, then N-chlorosuccinimide (1.6 g, 12 mmol) was added in three steps, and reaction was carried out for 4-6 hours while the room temperature was kept after adding was finished to finish TLC detection reaction. Reaction fluid was poured in 50 mL of water to implement quenching reaction. The reaction fluid was extracted with dichloromethane for three times, and organic phases were merged, and were washed with a saturated sodium bicarbonate solution, a saturated salt solution and water successively. Concentration was carried out after drying with anhydrous sodium sulfate, and an obtained grease crude product was recrystallized with ethyl acetate/n-hexane to obtain off-white solid AP26113 (I) 3.5 g, the yield was 66.3%, and FAB-MS m/z: 529 [M+H]$^+$, $^1$H NMR (CDCl3) 1.67 (m, 2H), 1.81 (s, 3H), 1.85 (s, 3H), 1.93 (m, 2H), 1.96 (m, 2H), 2.10 (m, 1H), 2.34 (s, 6H), 2.69 (m, 2H), 3.65 (m, 2H), 3.86 (s, 3H), 6.50 (m, 1H), 6.57 (m, 1H), 7.12 (m, 1H), 7.37 (m, 1H), 7.50 (m, 1H), 8.13 (m, 2H) and 8.64 (m, 1H).

It should be noted that the examples discussed above are merely for describing the technical concept and features of the invention, their objective is that those skilled in the art could understand the content of the invention and implement therefrom, and limitation to the patent scope of the invention cannot be made only by these examples. All equivalent changes or modifications according to the spirit of the invention should fall within the extent of protection of the invention.

What is claimed is:
1. A preparation method of an antitumor drug AP26113 (I),

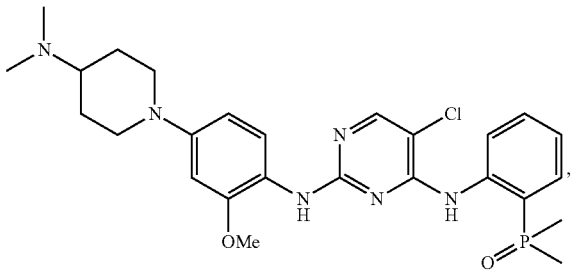

AP26113 (I)

comprising the following preparation steps:
  carrying out a cyclization reaction on N-[2-methoxyl-4 [4-(dimethyl amino)piperid-1-yl]aniline]guanidine and N,N-dimethylamino acrylate to prepare N2-[4-[4-(dimethyl amino)-1-piperidyl]-2-methoxyphenyl]amino-4 (1H)-pyrimidone;
  carrying out a condensation reaction on N2-[4-[4-(dimethyl amino)-1-piperidyl]-2-methoxyphenyl]amino-4 (1H)-pyrimidone and 4-(dimethyl phosphitylate)aniline in the presence of a condensating agent and an alkali accelerator to prepare N2-[4-[4-(dimethyl amino)-1-piperidyl]-2-methoxyphenyl]-N4-[2-(dimethyl phosphitylate)phenyl]-2,4-diaminopyrimidine; and
  carrying out a chlorination reaction on N2-[4-[4-(dimethyl amino)-1-piperidyl]-2-methoxyphenyl]-N4-[2-(dimethyl phosphitylate)phenyl]-2,4-diaminopyrimidine and a chlorinating agent to prepare AP26113 (I);
  wherein:
  the condensating agent of the condensation reaction is N,N'-dicyclohexylcarbodiimide, carbonyldiimidazole, N,N'-diisopropylcarbodiimide, 1-hydroxy-benzotriazole, 2-(1H-benzotriazole-1-yl)-1,1,3,3-tetramethyluronium tetrafluoroborate, O-(7-azabenzotriazol-1-yl)-N,N,N',N'-tetramethyluronium hexafluorophosphate, O-benzotriazol-1-yl-tetramethyluronium hexafluorophosphate or (benzotriazollyloxy)tris(dimethylamino) phosphonium hexafluophosphate.

2. The preparation method of AP26113 according to claim 1, wherein a molar ratio of N-[2-methoxyl-4[4-(dimethyl amino)piperid-1-yl]aniline]guanidine and the N,N-dimethylamino acrylate for the cyclization reaction is 1:1-2.

3. The preparation method of AP26113 according to claim 1, wherein a solvent of the cyclization reaction is methylbenzene, dimethylbenzene, dioxane, acetonitrile, N,N-dimethylformamide, N,N-dimethylacetamide or dimethylsulfoxide.

4. The preparation method of AP26113 according to claim 1, wherein the N,N-dimethylamino acrylate used for the cyclization reaction is N,N-dimethylaminomethyl acrylate or N,N-dimethylaminoethyl acrylate, and a temperature of the cyclization reaction is 50-150° C.

5. The preparation method of AP26113 according to claim 1, wherein the alkali accelerator of the condensation reaction is triethylamine, pyridine, 2,6-dimethyl pyridine, 4-dimethylaminopyridine, N-methylmorpholine, N-ethylmorpholine, diisopropylethylamine, 1,5-diazabicyclo[4.3.0]-non-5-ene, 1,8-diazabicyclo[5.4.0]-undeca-7-ene or 1,4-diazabicyclo-[2.2.2]octane.

6. The preparation method of AP26113 according to claim 1, wherein a solvent of the condensation reaction is methylbenzene, dimethylbenzene, ethyl acetate, isopropyl acetate, butyl acetate, chloroform, dimethylsulfoxide, N,N-dimethylformamide or acetonitrile; and a temperature of the condensation reaction is 0-120° C.

7. The preparation method of AP26113 according to claim 1, wherein the chlorinating agent of the chlorination reaction is N-chlorosuccinimide or 1,3-dichloro-5,5-dimethylhydantoin.

8. The preparation method of AP26113 according to claim 1, wherein the solvent of the chlorination reaction is tetrahydrofuran, dioxane, acetonitrile, dichloromethane, chloroform or methylbenzene; and a temperature of the chlorination reaction is 0-70° C.

9. The preparation method of AP26113 according to claim 1, wherein N-[2 methoxyl-4[4-(dimethyl amino)piperid-1-yl]aniline]guanidine (II) is prepared by carrying out a guanidination reaction on 2-methoxyl-4[4-(dimethyl amino) piperid-1-yl]aniline (B) and hydrogen cyanamide, a molar ratio of 2 methoxyl-4[4-(dimethyl amino)piperid-1-yl]aniline (B) and hydrogen cyanamide for the guanidination reaction is 1:1-2, a solvent of the guanidination reaction is benzene, methylbenzene, methanol, ethanol, N,N-dimethylformamide or dioxane, and a temperature of the guanidination reaction is 25-120° C.

10. A preparation method of an antitumor drug AP26113 (I),

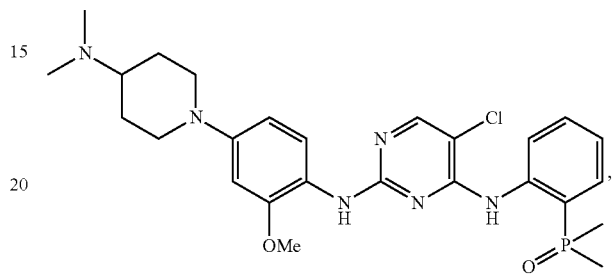

AP26113 (I)

comprising the following preparation steps:
  carrying out a cyclization reaction on N-[2-methoxyl-4 [4-(dimethyl amino)piperid-1-yl]aniline]guanidine and N,N-dimethylamino acrylate to prepare N2-[4-[4-(dimethyl amino)-1-piperidyl]-2-methoxyphenyl]amino-4 (1H)-pyrimidone;
  carrying out a condensation reaction on N2-[4-[4-(dimethyl amino)-1-piperidyl]-2-methoxyphenyl]amino-4 (1H)-pyrimidone and 4-(dimethyl phosphitylate)aniline in the presence of a condensating agent and an alkali accelerator to prepare N2-[4-[4-(dimethyl amino)-1-piperidyl]-2-methoxyphenyl]-N4-[2-(dimethyl phosphitylate)phenyl]-2,4-diaminopyrimidine; and
  carrying out a chlorination reaction on N2-[4-[4-(dimethyl amino)-1-piperidyl]-2-methoxyphenyl]-N4-[2-(dimethyl phosphitylate)phenyl]-2,4-diaminopyrimidine and a chlorinating agent to prepare AP26113 (I);
  wherein:
  the alkali accelerator of the condensation reaction is triethylamine, pyridine, 2,6-dimethyl pyridine, 4-dimethylaminopyridine, N-methylmorpholine, N-ethylmorpholine, diisopropylethylamine, 1,5-diazabicyclo [4.3.0]-non-5-ene, 1,8-diazabicyclo[5.4.0]-undeca-7-ene or 1,4-diazabicyclo-[2.2.2]octane.

11. A preparation method of an antitumor drug AP26113 (I),

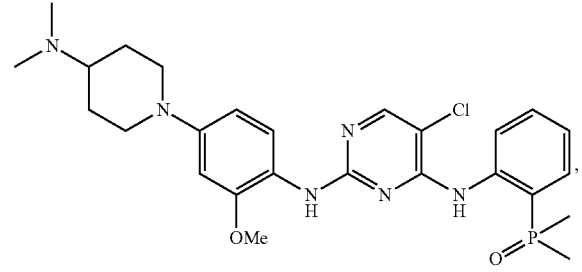

AP26113 (I)

comprising the following preparation steps:

carrying out a cyclization reaction on N-[2-methoxyl-4[4-(dimethyl amino)piperid-1-yl]aniline]guanidine and N,N-dimethylamino acrylate to prepare N2-[4-[4-(dimethyl amino)-1-piperidyl]-2-methoxyphenyl]amino-4(1H)-pyrimidone;

carrying out a condensation reaction on N2-[4-[4-(dimethyl amino)-1-piperidyl]-2-methoxyphenyl]amino-4(1H)-pyrimidone and 4-(dimethyl phosphitylate)aniline in the presence of a condensating agent and an alkali accelerator to prepare N2-[4-[4-(dimethyl amino)-1-piperidyl]-2-methoxyphenyl]-N4-[2-(dimethyl phosphitylate)phenyl]-2,4-diaminopyrimidine; and carrying out a chlorination reaction on N2-[4-[4-(dimethyl amino)-1-piperidyl]-2-methoxyphenyl]-N4-[2-(dimethyl phosphitylate)phenyl]-2,4-diaminopyrimidine and a chlorinating agent to prepare AP26113 (I); wherein:

the chlorinating agent of the chlorination reaction is N-chlorosuccinimide or 1,3-dichloro-5,5-dimethylhydantoin.

12. The preparation method of AP26113 according to claim 10, wherein a molar ratio of N-[2-methoxyl-4[4-(dimethyl amino)piperid-1-yl]aniline]guanidine and the N,N-dimethylamino acrylate for the cyclization reaction is 1:1-2.

13. The preparation method of AP26113 according to claim 10, wherein a solvent of the cyclization reaction is methylbenzene, dimethylbenzene, dioxane, acetonitrile, N,N-dimethylformamide, N,N-dimethylacetamide or dimethylsulfoxide.

14. The preparation method of AP26113 according to claim 10, wherein the N,N-dimethylamino acrylate used for the cyclization reaction is N,N-dimethylaminomethyl acrylate or N,N-dimethylaminoethyl acrylate, and a temperature of the cyclization reaction is 50-150° C.

15. The preparation method of AP26113 according to claim 10, wherein a solvent of the condensation reaction is methylbenzene, dimethylbenzene, ethyl acetate, isopropyl acetate, butyl acetate, chloroform, dimethylsulfoxide, N,N-dimethylformamide or acetonitrile; and a temperature of the condensation reaction is 0-120° C.

16. The preparation method of AP26113 according to claim 11, wherein a molar ratio of N-[2-methoxyl-4[4-(dimethyl amino)piperid-1-yl]aniline]guanidine and the N,N-dimethylamino acrylate for the cyclization reaction is 1:1-2.

17. The preparation method of AP26113 according to claim 11, wherein a solvent of the cyclization reaction is methylbenzene, dimethylbenzene, dioxane, acetonitrile, N,N-dimethylformamide, N,N-dimethylacetamide or dimethylsulfoxide.

18. The preparation method of AP26113 according to claim 11, wherein the N,N-dimethylamino acrylate used for the cyclization reaction is N,N-dimethylaminomethyl acrylate or N,N-dimethylaminoethyl acrylate, and a temperature of the cyclization reaction is 50-150° C.

19. The preparation method of AP26113 according to claim 11, wherein a solvent of the condensation reaction is methylbenzene, dimethylbenzene, ethyl acetate, isopropyl acetate, butyl acetate, chloroform, dimethylsulfoxide, N,N-dimethylformamide or acetonitrile; and a temperature of the condensation reaction is 0-120° C.

* * * * *